US 8,216,192 B2

(12) United States Patent
Burroughs et al.

(10) Patent No.: US 8,216,192 B2
(45) Date of Patent: Jul. 10, 2012

(54) MODULE FOR A MEDICATION INJECTION DEVICE

(75) Inventors: Andrew Christopher Burroughs, Kenosha, WI (US); Rodney Hal Monson, Waukegan, IL (US); Volker Roos, Unterfohring (DE)

(73) Assignee: Eli Lilly and Company, Indianapolis, IN (US)

( * ) Notice: Subject to any disclaimer, the term of this patent is extended or adjusted under 35 U.S.C. 154(b) by 700 days.

(21) Appl. No.: 12/301,529

(22) PCT Filed: May 9, 2007

(86) PCT No.: PCT/US2007/068556
§ 371 (c)(1),
(2), (4) Date: Feb. 26, 2009

(87) PCT Pub. No.: WO2007/143323
PCT Pub. Date: Dec. 13, 2007

(65) Prior Publication Data
US 2009/0227958 A1 Sep. 10, 2009

Related U.S. Application Data

(60) Provisional application No. 60/809,200, filed on May 30, 2006.

(51) Int. Cl.
*A61M 5/32* (2006.01)
(52) U.S. Cl. ..................................................... 604/201
(58) Field of Classification Search .................. 604/518, 604/520, 82, 232, 233, 201
See application file for complete search history.

(56) References Cited

U.S. PATENT DOCUMENTS

| 3,563,373 | A | 2/1971 | Paulson |
| 4,927,423 | A | 5/1990 | Malmborg |
| 5,137,511 | A | 8/1992 | Reynolds |
| 6,637,470 | B2 | 10/2003 | Reihl et al. |
| 6,638,244 | B1 | 10/2003 | Reynolds |
| 6,780,171 | B2 * | 8/2004 | Gabel et al. .................. 604/181 |
| 2001/0051793 | A1 | 12/2001 | Weston |

FOREIGN PATENT DOCUMENTS

| WO | WO 00/15281 | 3/2000 |
| WO | WO 02/05878 | 1/2002 |
| WO | WO 03/090822 | 11/2003 |
| WO | WO 2005/097237 | 10/2005 |
| WO | WO 2006/014901 | 2/2006 |
| WO | WO 2006/058435 | 6/2006 |

* cited by examiner

*Primary Examiner* — Kevin C Sirmons
*Assistant Examiner* — Brandy C Scott
(74) *Attorney, Agent, or Firm* — Edward J. Prein

(57) ABSTRACT

A medication and needle module (20) for an injection device. The module (20) includes a housing (22) including a first portion (39) and a second portion (38) detachably connected together, the second housing portion having a periphery complementarily shaped with a cavity (154) in the injection device (150) to be loadable therein, a primary container (120) within the first housing portion and including a medication filled reservoir (124), a secondary container (70) within the second housing portion and including a medication tillable reservoir, a needle cassette (60) rotatably mounted within the second housing portion and including a plurality of delivery needles (64), and a transfer needle assembly (100) within the housing. The detachability of the second housing portion from the first housing portion permits the second housing portion with the secondary container and the needle cassette to be loaded as a unit independently of the first housing portion into the injection device cavity for use.

6 Claims, 6 Drawing Sheets

MODULE FOR A MEDICATION INJECTION DEVICE

This is the national phase application, under 35 USC 371, for PCT/US2007/068556, filed 9 May 2007, which claims the benefit, under 35 USC 119(e), of U.S. provisional applications 60/809,200 filed 30 May 2006.

BACKGROUND OF THE INVENTION

The present invention pertains to medical devices, and, in particular, to medicine containers and needles for medication injection devices.

A wide variety of medication injection devices are available which allow people, such as patients or health care professionals, to administer pharmaceuticals to themselves or others. Many of these devices are considered reusable, but utilize disposable injection needles as well as disposable cartridges, which cartridges each hold one or more doses of the desired pharmaceutical.

One problem associated with some injection devices is the management of the various pieces necessary to prepare or load such a device for operation. As the needle of the injection device may be recommended to be replaced after each use, constantly keeping track of and handling needles may be inconvenient for a user. Still further, at least one injection device may require filling of its cartridge with medication from a primary container prior to use, which transfer may require a handling of various components separately from the needles which some users may find burdensome.

Thus, it would be desirable to provide an improvement that facilitates the proper loading and use of a medication injection device.

BRIEF SUMMARY OF THE INVENTION

In one form thereof, the present invention provides a medication and needle module for an injection device, including: a housing including a first portion and a second portion detachably connected together, the second housing portion having a periphery complementarily shaped with a cavity in the injection device to be loadable therein, a primary container within the first housing portion and including a medication filled reservoir, a secondary container within the second housing portion and including a medication fillable reservoir, a needle cassette rotatably mounted within the second housing portion and including a plurality of delivery needles, each one of the delivery needles independently being placeable in fluid communication with the medication fillable reservoir of the secondary container at a different angular orientation of the needle cassette within the second housing portion, and a transfer needle assembly within the housing and including a cannula for fluid communication between the medication filled reservoir of the primary container and the medication fillable reservoir of the secondary container. The detachability of the second housing portion from the first housing portion permits the second housing portion with the secondary container and the needle cassette to be loaded as a unit independently of the first housing portion into the injection device cavity for use.

One advantage of the present invention is that a medication and needle cassette module may be provided that is handled as a single unit but includes sufficient medication and single use needles for a given number, such as one weeks worth, of uses, and which medication and needles are exhausted simultaneously.

Another advantage of the present invention is that a medication and needle cassette module may be provided that includes a needle cassette and a secondary container loadable together into an injection device, as well as a primary container used to fill the secondary container, all in a common package that makes transport and handling convenient for a user.

Another advantage of the present invention is that a medication and needle cassette module may be provided that includes a shuttling mechanism for transferring of medication from a primary container to a secondary container with a needle cassette loadable into a medication injection device.

Yet another advantage of the present invention is that a medication and needle cassette module may be provided that has a portion that is easily removable as a unit from a medication injection device for storage in, for example, a refrigerator, and then easily reinstalled as a unit when needed.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
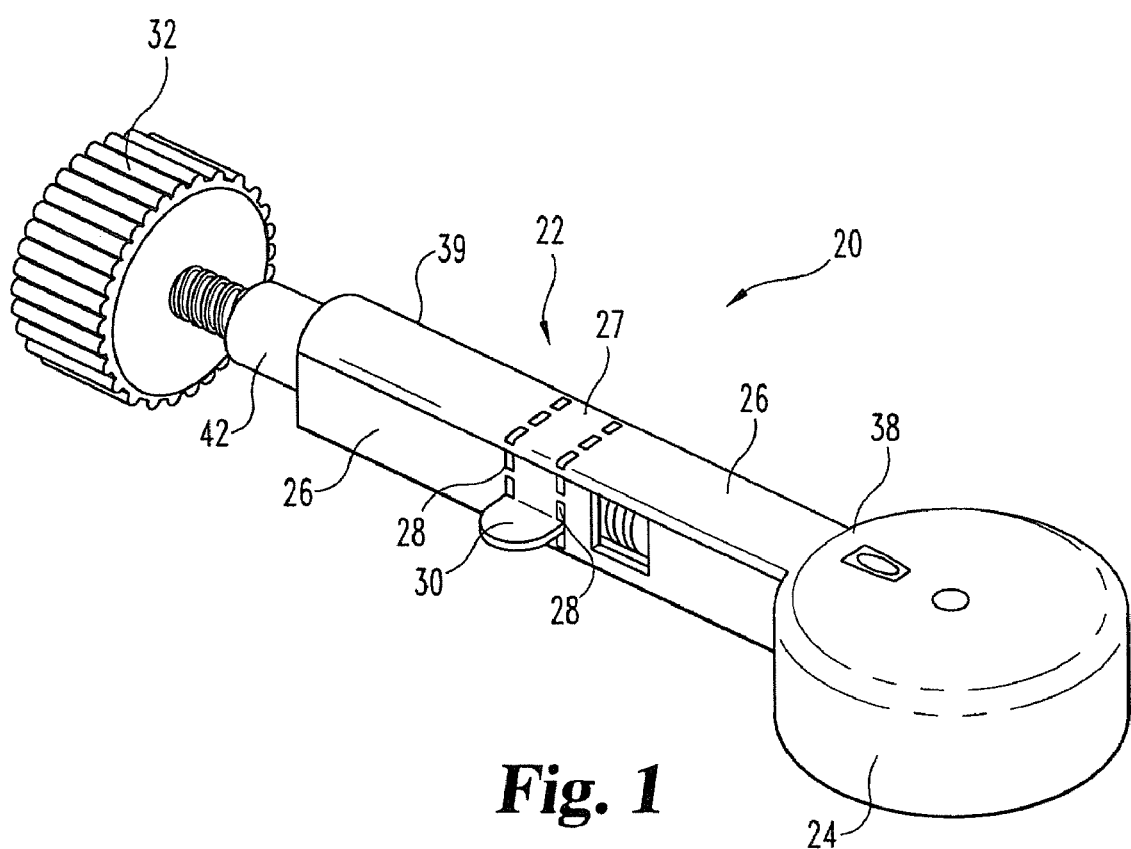
FIG. 1 is a front perspective view of an exemplary medication and needle cassette module of the present invention.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

With initial reference to FIG. 1, there is shown a first embodiment of a medication and needle cassette module of the present invention, which module is generally designated 20. Module 20 is provided as an assembled unit, including a primary container, a secondary container, and a needle cassette, which can be carried and used in a convenient and simple manner. Module 20 is suited for use with a medication injection device structured to be compatible therewith, which device may generally be of a type disclosed in International Publication Number WO 2005/097237. As module 20 may be used in various medication injection devices which are designed to operate in different ways, module 20 is therefore described herein with only limited reference to such devices, and such devices themselves do not form a part of the instant invention.

Module 20 is shown in a front perspective view in FIG. 1 arranged as may be provided to the end user by the manufacturer. In such arrangement, module 20 has yet to have been operated by a user to transfer medication from the primary container to the secondary container within the housing. For the shown module 20, front and rear, and forward and rearward, refer to relative locations on the module, wherein a direction of travel of the primary container piston during use to fill the secondary container is considered a forward travel. These references, as well as any other directional references in this detailed description with respect to the Figures, such as top or bottom, are intended for convenience of description, and by itself does not limit the present invention or any of its components to any particular positional or spatial orientation.

Module 20 includes a protective housing or outer casing, generally designated 22, formed with a cylindrical, needle cassette-enclosing region 24 and a squarer, medication containers-enclosing region 26 radially protruding from cylindrical region 24. Housing 22 is formed of a plastic material, such as polypropylene, polyethylene or others depending on the requirements dictated by use or manufacture. Housing 22 is designed to be disconnectable into multiple pieces or portions so as to allow one housing portion 38, with its contents, to be loaded into an injection device, and another housing portion 39, with its contents, to be disposed of after supply. In the shown embodiment, such disconnectabilty into two pieces is provided by a tear strip therebetween, but other methods of disconnection may be employed. The tear strip 27 is formed by a middle area of the housing region 26, such as defined by a parallel pair of score lines 28 that extend circumferentially around the housing and which flank a projecting gripping tab 30 integrally formed with the housing. A manually operable, twistable knob 32 is shown located at the rear end of the housing region 26.

Figure 2:
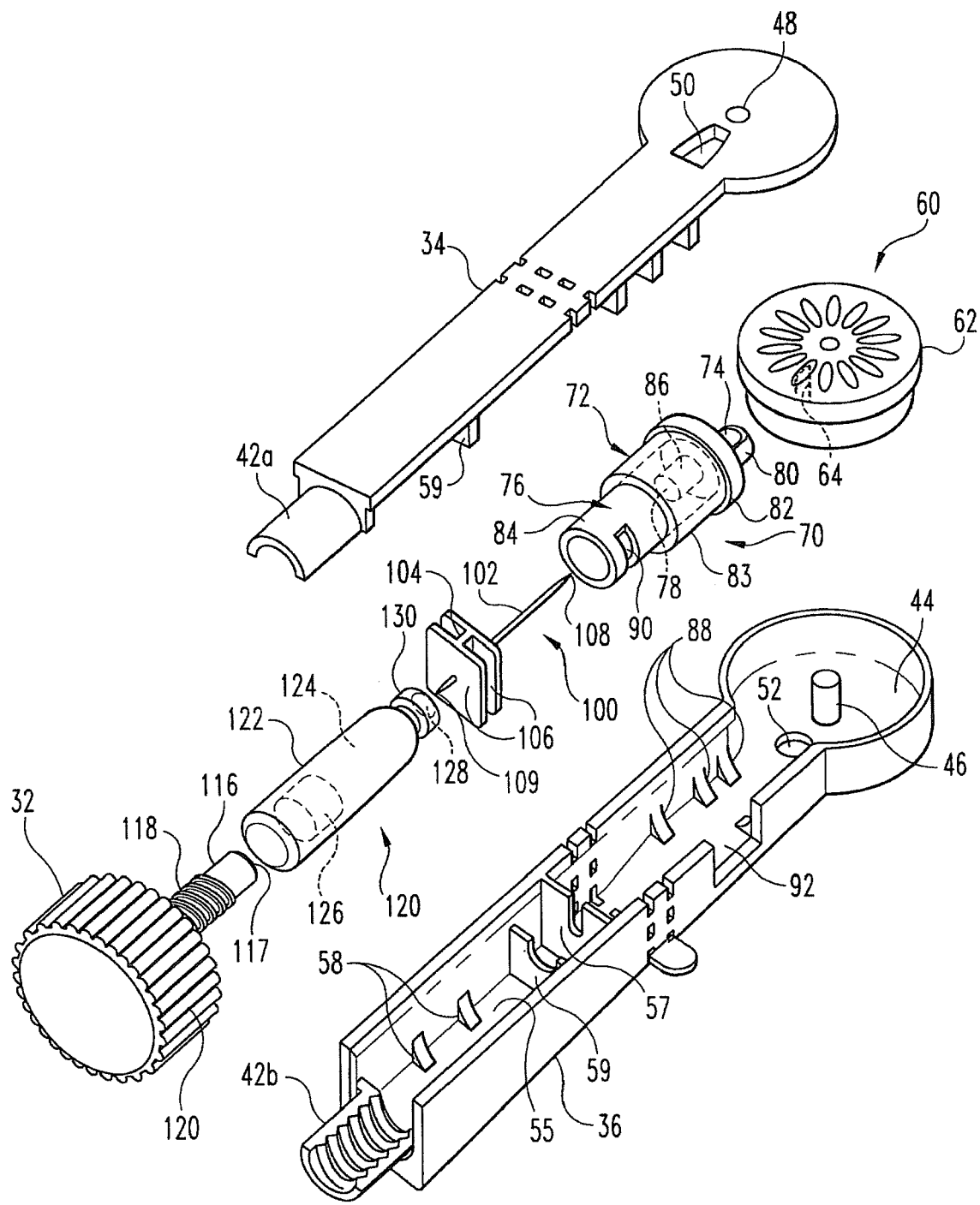
FIG. 2 is an exploded, rear perspective view of the medication and needle cassette module of FIG. 1.

With additional reference to the exploded view of module 20 in FIG. 2, the housing 22 holds a needle cassette 60, a secondary medication container 70, a transfer needle assembly 100, and a primary medication container 120. Housing 22 is formed of a top piece 34 and a complementary bottom piece 36 that are fixedly mated together, such as with adhesives, during manufacturing assembly. Collar sections 42a and 42b of housing pieces 34 and 36, respectively, form a tubular collar 42 that is internally threaded. Other housing piece constructions that achieve a suitable overall shape and openings may be employed.

Housing portion 38 includes an internal hollow 44 within its cylindrical region 24 having an upstanding post 46 centered therein. Post 46 serves as an axis about which the needle cassette 60 is rotatably indexable within the housing portion. An opening 48 in top piece 34 accommodates the axle post 46. An aperture 50 radially spaced and extending away from opening 48 is sized and shaped to accommodate a mechanism of the injection device used to operate the individual needles of the needle cassette. An opening 52 in housing bottom piece 36 allows passage of a user skin-penetrating needle tip from the needle cassette. Other not shown openings may also be provided in housing portion 38 around the needle cassette as may be desirable, such as to allow an indexing mechanism of the injection device to selectively rotate cassette 60 about the axle post 46 during operation of the device, or to allow a sensing mechanism of the injection device to sense unused needles in the cassette.

The needle cassette 60 is shown as comprised of a carousel assembly 62 that supports a plurality of J-shaped delivery needles, only one of which is more fully shown at 64. Each of needles 64 includes septum-piercing and skin-piercing tips that are parallel and point in the same direction, and each needle is axially movable relative to carousel assembly 62 during its respective operation. The needle cassette, which generally may be of a type disclosed in International Publication Number WO 2005/097237, is only shown abstractly and briefly described herein as other specifics are not material to the present invention. The shown needle cassette includes fourteen needles as its plurality, making the module 20 highly suitable to provide a one week supply of a twice-a-day drug. Different numbers of needles naturally may be employed depending on the intended use of the module 20. The needle cassette 60 is rotatably mounted within housing portion 38 to allow the needles to be moved into a proper operational position with respect to the secondary container. During its use to inject, each one of the delivery needles 64, at a different angular orientation of the needle cassette 60 within the housing portion 38, is independently placeable in fluid communication with a medication fillable reservoir of the secondary container.

The secondary or medication fillable container 70 housed within housing portion 38 is shown as a cartridge comprised of a barrel assembly 72 that includes an injection needle pierceable dispensing septum 74, and a shiftable piston 76 that includes a transfer needle pierceable filling septum 78. This cartridge, which generally may be of a type disclosed in International Publication Number WO 2006/014901, is also only shown abstractly and briefly described herein as other specifics are not material to the present invention. Septum 74 is located on a laterally facing area of a protuberance 80 integrally formed with a disc portion 82 of the barrel assembly 72, and seals the forward end of the medication fillable, variable volume reservoir of the assembly 72. Septum 74 is penetrable by one tip of each delivery needle 64 when properly positioned, but in alternate embodiments may be a valve which is accessed by a complementary feature of each needle.

The rearward end of the reservoir is sealed by piston 76 that includes a tubular, cylindrical body 84 that sealably engages, such as via circumferential O-rings, the interior wall of the barrel body 83 that may be plastic or glass or glass-lined. Septum 78 sealingly covers the rearward end of a tube 86 within and integrally formed with body 84, the forward end of which tube opens into the medication-fillable, variable volume reservoir of the assembly 72. The piston body 84 is shown including a slot 90 that is accessible through a side opening 92 in housing bottom piece 36 by a mechanism of an injection device used to move the piston when installed within that injection device.

Secondary cartridge 70 is supported within housing 22 forward of tear strip 27 by a series of ribs 88 formed in the interior of housing portion 38. Ribs 88 radially locate cartridge 70 and also axially secure cartridge 70 by being spaced to accommodate a circumferential lip of the disc portion 82 inserted therebetween during module assembly. Others means of securing the cartridge, including adhesives, may be employed.

Housing portion 39 includes an interior hollow 55 in which is housed the medication-filled primary container and the base of the transfer needle assembly 100. Needle assembly 100 is provided by a double ended needle or cannula 102 that is fixedly mounted within a hub 104 formed with a pair of plates 106 that are transverse to cannula 102 and separated by a connecting span of the hub to define an axial space. Needle assembly 100 is installed into the housing 22 during module assembly such that hub plates 106 can slide in the axial space between slotted shoulder 57 formed in housing bottom piece 36 and shoulders 59. Cannula 102 axially extends through the slot of shoulder 57. Needle assembly 100 is friction fit in housing 22, such as with detents in the housing that engage plates 106, so as to be held in an assembled position prior to use and then be axially shiftable during medication transfer.

The primary container 120 housed within housing portion 39 is shown as a cartridge of a conventional size and shape, and includes a barrel 122 made of glass, a medication-filled reservoir 124 within the barrel, a piston 126, a septum 128 and a cap 130. Although shown as a standard 3 ml cartridge, to limit wastage the reservoir 124 need only be filled with as much medication as expected to be required within the secondary cartridge 70 for its intended use. Piston 126 seals the rearward end of reservoir 124 and is axially slidably and sealably engaged with the barrel interior wall. Septum 128 is held by a cap 130 that is secured to a stepped-down diameter neck portion of the barrel, and septum 128 seals the forward end of reservoir 124. Ribs 58 in the housing pieces support the cartridge barrel 122. Recessed shoulders 59 allow axial passage of cap 130, but are sized to limit the forward movement of cartridge 70. Cartridge 70 is friction fit in housing 22 so as to be held in an assembled position prior to use and then be axially shiftable during medication transfer.

The transfer knob 32 includes a central shaft 116 that is sized to freely fit within cartridge barrel 122 such that the shaft forward end 117 can directly abut piston 126. Shaft 116 extends forward from the grip region 120 of knob 32 sufficiently to allow piston 126 to be advanced to fill the secondary container appropriately. An externally threaded region 118 of shaft 116 threadedly engages collar 42 to be screwable into housing 22. The knob grip region 120 is shown knurled to facilitate being gripped by a user. In alternate embodiments, different means for advancing piston 126 can be substituted for knob 32 with its thread shaft within the scope of the invention, such as a manually driven plunger slidably mounted to the housing.

The structure of module 20 will be further understood in view of the following description of a use thereof. A user will obtain module 20 arranged as shown in FIG. 1. While holding housing 22 in one hand and gripping knob 32 in the other, the user twists knob 32 relative to the housing to advance shaft 116 farther into the housing and push the piston 126 forward, which advancement first drives cartridge 120 forward until cap 130 abuts plate 106 and needle tip 109 penetrates septum 128, after which time further advancement of shaft 116 causes the needle assembly to moves forward until the forward plate 106 abuts shoulder 57 and needle tip 108 penetrates septum 78, putting the medication filled reservoir of container 120 in fluid communication with the medication fillable reservoir of container 70. As shaft 116 continues to be advanced, cartridge piston 126 is driven forward in barrel 122, resulting in medication in reservoir 124 being forced through needle 102 into the fillable reservoir of secondary container 70 so as to move the secondary container piston rearward by fluid pressure. Knob 32 is to be screwed in far enough to fully transfer the required medication to the secondary container, such as indicated to the user by the forward face of the knob abutting the housing or other stop means. Then, by gripping tab 30 and pulling around the housing, the user can remove tear strip 27 to divide the housing into the housing portion 39 that contains used supply components, herein together called the module supply portion, and the housing portion 38 that contains the now filled secondary container and the needle cassette, herein together called the module loadable portion.

The module supply portion may then be moved away from the module loadable portion and properly disposed of as a unit in the normal course, with the user taking care to stay clear of the forward tip of the transfer needle projecting therefrom. In an alternate embodiment, a shielding feature for the projecting needle tip may be the employed.

Figure 3:
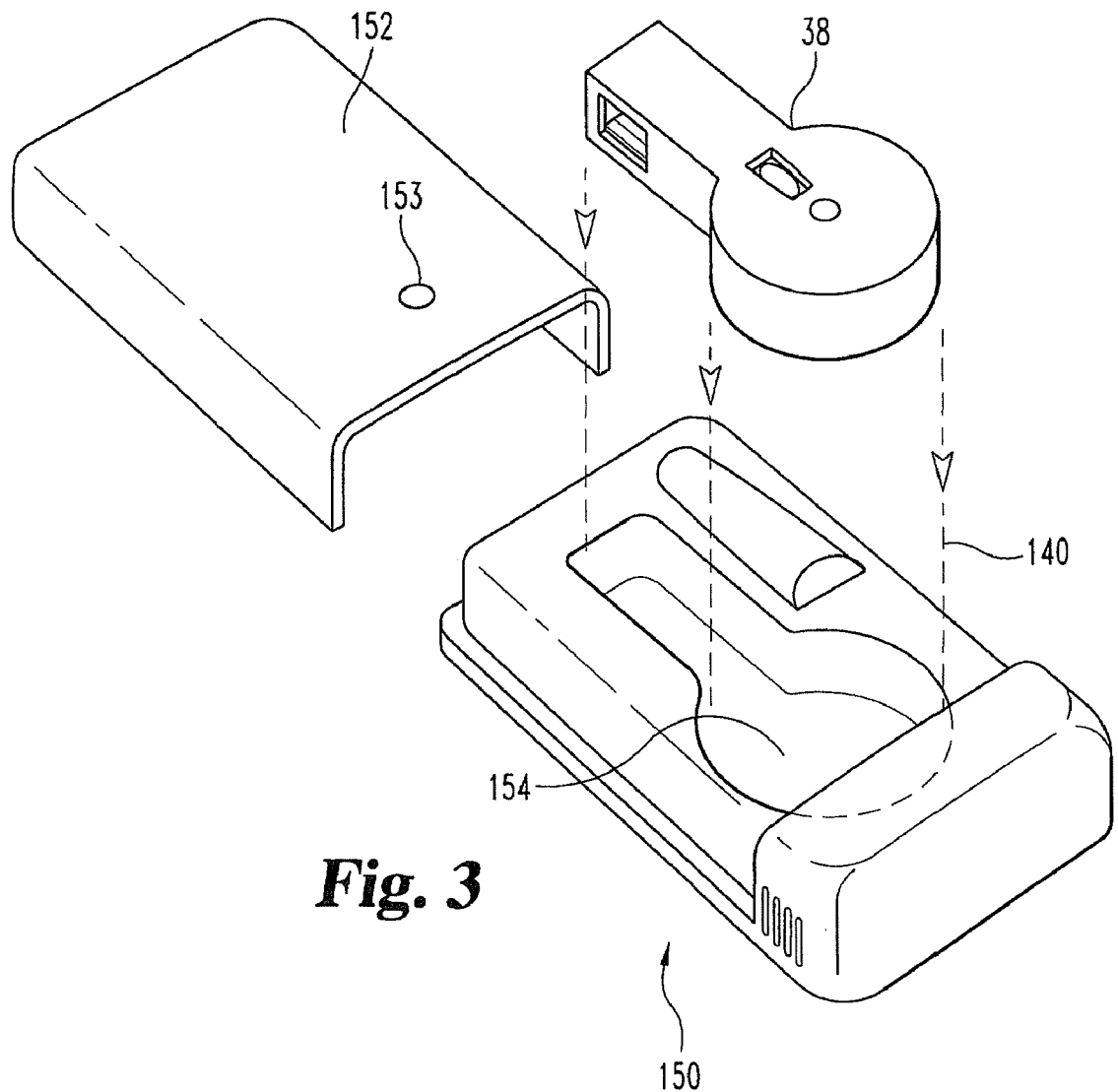
FIG. 3 is a perspective view of the loadable portion of the medication and needle cassette module of FIG. 1, after having the supply portion of the module detached and removed from view, being inserted into an abstractly shown medication injection device.

The module loadable portion then can be inserted as indicated at 140 in FIG. 3 into a medication injection device usable therewith, which device is abstractly shown at 150. Device 150 is shown in FIG. 3 with its housing cover 152 slid off to expose a recess or cavity 154. Housing portion 38 has a periphery complementarily shaped with cavity 154 to be loadable therein. When the module loadable portion is enclosed within device 150, the housing portion 38 is not movable therein except for possibly small movement associated with tolerances. Housing cover 152 includes a hole 153 through which each injection needle 64 can be separately projected during use.

Figure 4:
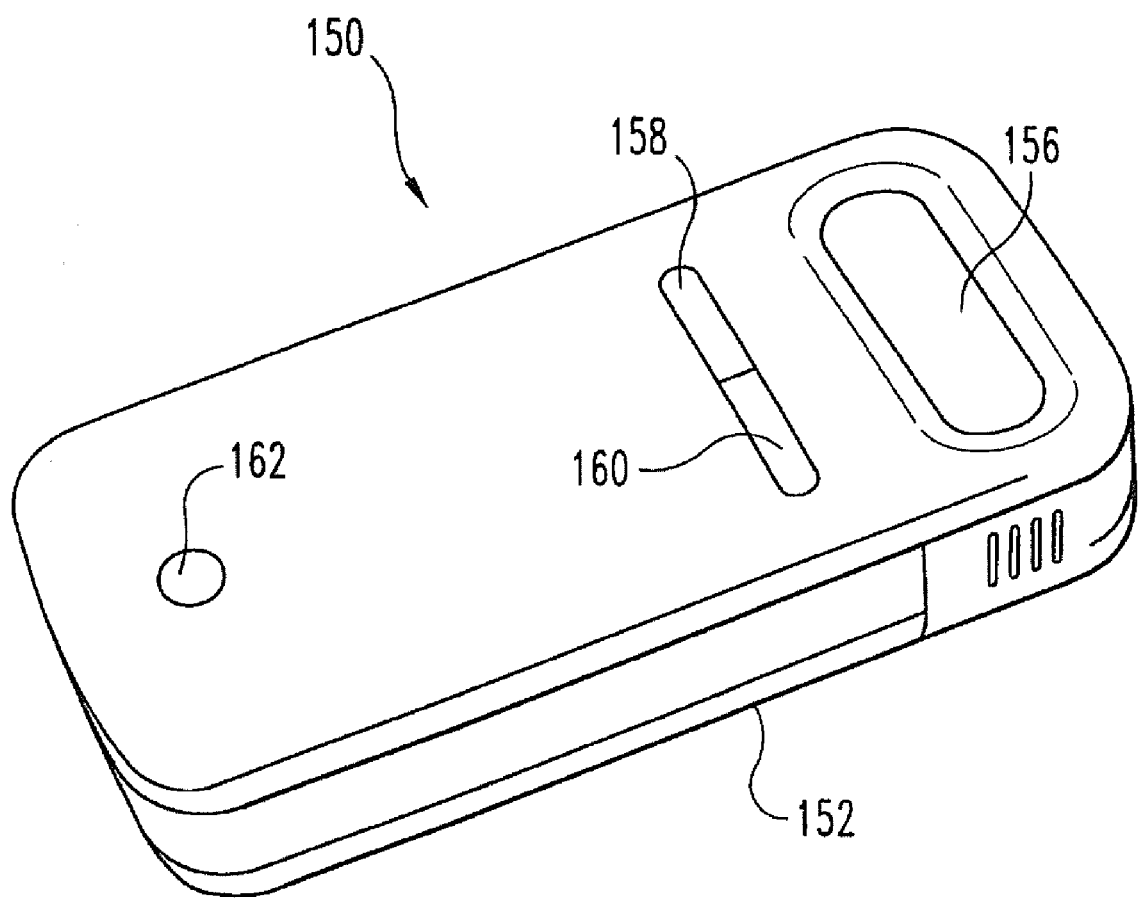
FIG. 4 is a perspective view of the injection device of FIG. 3 after being loaded, closed and turned over.

FIG. 4 shows device 150 after cover 152 is slid back on to capture the loadable module portion inserted therein, and the device has been turned over. Device 150 is shown simply including an activation button 156 that a user can press to operate the device, illuminatable indicator bars 158 and 160 that can indicate, for example, interaction cues or status of needles or medication, and a power button 162.

Figure 5:
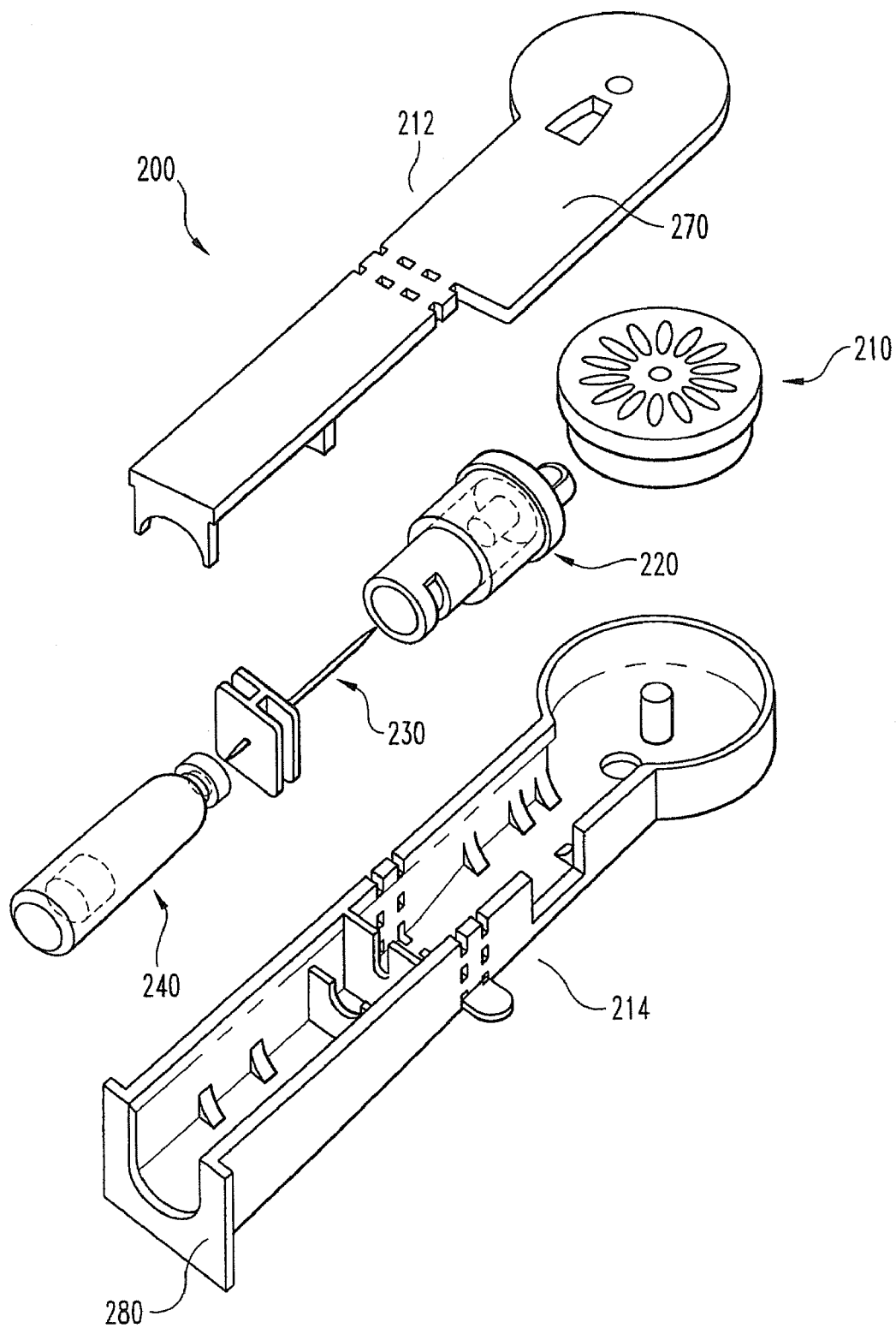
FIG. 5 is a rear perspective view of another exemplary medication and needle cassette module of the present invention.
Figure 6:
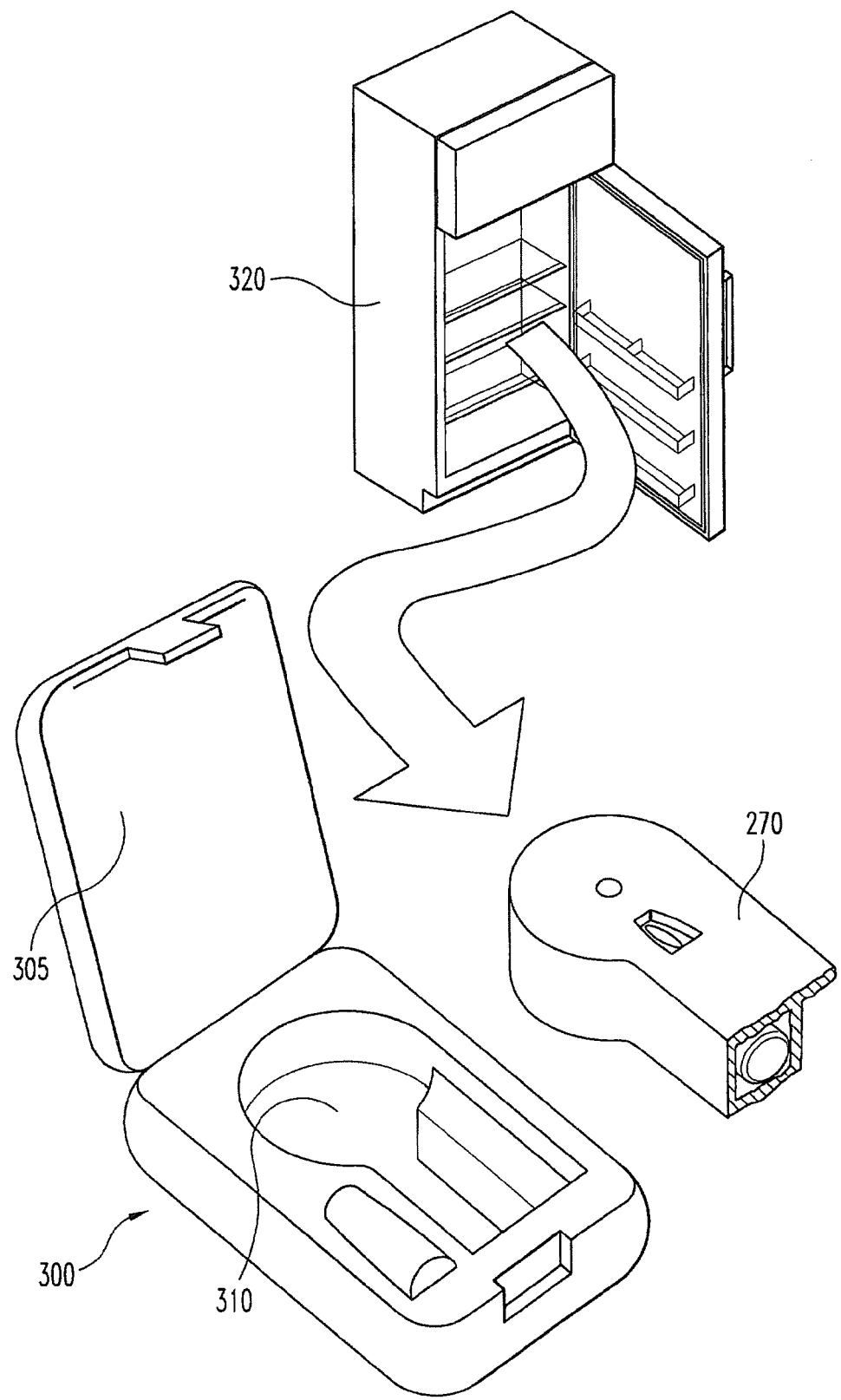
FIG. 6 is a rear perspective view of a loadable portion of the medication and needle cassette module of FIG. 5, with the supply portion of the module detached and removed from view, while being moved from a refrigerator for re-insertion into an abstractly shown injection device.

Referring now to FIGS. 5 and 6, there is shown an alternate embodiment of a medication and needle cassette module of the present invention. The module, generally designated 200, is similar in most respects to module 20 shown and described with respect to FIGS. 1-4 above, and includes a needle cassette 210, a secondary medication container 220, a transfer needle assembly 230, and a primary medication container 240 all of which are housed within a housing formed of a top piece 212 and a mating bottom piece 214. Module 200 differs from module 20 in that it includes an overhanging flange 270, as well as a retaining lip 280 instead of the threaded collar with transfer knob of module 20. Although flange 270 and lip 280 are shown provided together in this embodiment, each may be separately used in different embodiments.

Flange 270 may aid in orienting the module properly within the injection device described below. Retaining lip 280 at the rearward end of the module supply portion is adapted to seat within a groove in a not shown transfer accessory that is shaped to receive the entire module shown in FIG. 5. When module 200 is so received by the transfer accessory, a motorized or manually powered drive member of the accessory can be actuated or operated to ultimately advance the primary cartridge piston to force medication through the transfer needle into the secondary container. After the module is removed from such an accessory, it can be separated into its two housing portions, with the module supply portion being discarded and the module loadable portion being inserted into an injection device. One such injection device is shown abstractly in FIG. 6.

The device 300 includes a pivoting housing cover 305 which when opened reveals the cavity 310 into which the module loadable portion can be dropped. FIG. 6 further shows the filled module loadable portion being removed from a refrigerator 320. The module loadable portion can fit into a complementary tray which fits in the refrigerator between uses.

While this invention has been shown and described as having preferred designs, the present invention may be modified within the spirit and scope of this disclosure. For example, while the containers are described as cartridges with movable pistons, the invention can be used with other types of containers, such as collapsible ones. Further, the invention may be used with differently designed cartridges, such as that account for the septum in the secondary container in a fashion that does not require a tube section within the piston body, and further can use a transfer needle that does not move and instead pierces the septums during module assembly. Still further, with modification to the housing and/or the secondary cartridge piston, in an alternate embodiment the separation of the housing into its two portions after medication transfer may be accomplished by the fluid transfer means inparting sufficient hydraulic pressure to the secondary cartridge to cause that cartridge piston to act on the housing to break the connection between the housing portions. This application is therefore intended to cover any variations, uses or adaptations of the invention using its general principles. Further, this application is intended to cover such departures from the present disclosure as come within known or customary practice in the art to which this invention pertains.

We claim:

1. A medication and needle module for an injection device, comprising:
    a housing including a first portion and a second portion detachably connected together, said second housing portion having a periphery complementarily shaped with a cavity in the injection device to be loadable therein;
    a primary container within said first housing portion and including a medication filled reservoir;
    a secondary container within said second housing portion and including a medication fillable reservoir;
    a needle cassette rotatably mounted within said second housing portion and including a plurality of delivery needles, each one of said delivery needles independently being placeable in fluid communication with said medication fillable reservoir of said secondary container at a different angular orientation of said needle cassette within said second housing portion;
    a transfer needle assembly within said housing and including a cannula for fluid communication between said medication filled reservoir of said primary container and said medication fillable reservoir of said secondary container;
    whereby the detachability of said second housing portion from said first housing portion permits said second housing portion with said secondary container and said needle cassette to be loaded as a unit independently of said first housing portion into the injection device cavity for use, wherein said primary container comprises a cartridge including a body, a movable piston and a septum, said medication filled reservoir defined by said body between said movable piston and said septum, said septum at a forward end of said body for piercing by a first end of said cannula.

2. The medication and needle module of claim 1 wherein said secondary container comprises a cartridge including a body, and a movable piston with a septum which defines a rear end of said medication fillable reservoir, said septum of said piston for piercing by a second end of said cannula.

3. The medication and needle module of claim 2 wherein said cannula is straight and aligned with said primary container and said secondary container.

4. A medication and needle module for an injection device, comprising:
    a housing including a first portion and a second portion detachably connected together, said second housing portion having a periphery complementarily shaped with a cavity in the injection device to be loadable therein;
    a primary container within said first housing portion and including a medication filled reservoir;
    a secondary container within said second housing portion and including a medication fillable reservoir;
    a needle cassette rotatably mounted within said second housing portion and including a plurality of delivery needles, each one of said delivery needles independently being placeable in fluid communication with said medication fillable reservoir of said secondary container at a different angular orientation of said needle cassette within said second housing portion;
    a transfer needle assembly within said housing and including a cannula for fluid communication between said medication filled reservoir of said primary container and said medication fillable reservoir of said secondary container;
    whereby the detachability of said second housing portion from said first housing portion permits said second housing portion with said secondary container and said needle cassette to be loaded as a unit independently of said first housing portion into the injection device cavity for use, wherein said housing comprises a tear strip between said first and second housing portions which when removed detaches said first housing portion from said second housing portion.

5. The medication and needle module of claim 1 further comprising means attached to a rearward end of said housing first portion for advancing said movable piston to force medication from said medication filled reservoir to said medication fillable reservoir.

6. The medication and needle module of claim 5 wherein said advancing means comprises a manually operable knob with a shaft that screws through a threaded opening in said housing first portion to drive said movable piston.

* * * * *